(12) United States Patent
Karlsson et al.

(10) Patent No.: US 10,258,412 B2
(45) Date of Patent: Apr. 16, 2019

(54) METHOD AND NODE FOR MANUFACTURING A SURGICAL KIT FOR CARTILAGE REPAIR

(71) Applicant: EPISURF IP-MANAGEMENT AB, Stockholm (SE)

(72) Inventors: Anders Karlsson, Kävlinge (SE); Richard Lilliestråle, Stockholm (SE); Nina Bake, Lidingö (SE)

(73) Assignee: EPISURF IP-MANAGEMENT AB, Stockholm (SE)

( * ) Notice: Subject to any disclaimer, the term of this patent is extended or adjusted under 35 U.S.C. 154(b) by 0 days.

(21) Appl. No.: 15/417,657

(22) Filed: Jan. 27, 2017

(65) Prior Publication Data
US 2017/0135769 A1 May 18, 2017

Related U.S. Application Data

(63) Continuation of application No. 15/116,829, filed as application No. PCT/EP2014/052417 on Feb. 7, 2014.

(51) Int. Cl.
*A61B 34/10* (2016.01)
*A61F 2/30* (2006.01)
(Continued)

(52) U.S. Cl.
CPC .............. *A61B 34/10* (2016.02); *A61B 5/055* (2013.01); *A61B 6/032* (2013.01); *A61B 6/037* (2013.01);
(Continued)

(58) Field of Classification Search
CPC ........... A61B 34/10; A61B 8/00; A61B 6/037; A61B 6/032; A61B 5/055;
(Continued)

(56) References Cited

U.S. PATENT DOCUMENTS

| 5,741,215 A | 4/1998 | D'Urso |
| 7,239,908 B1 | 7/2007 | Alexander et al. |

(Continued)

FOREIGN PATENT DOCUMENTS

| CN | 1780594 A | 5/2006 | |
| EP | 2389899 A1 * | 11/2011 | ......... A61B 17/1675 |

(Continued)

OTHER PUBLICATIONS

First Chinese Office Action dated Apr. 1, 2017 issued in corresponding Chinese patent application No. 2014800748646 (7 pages) and its English-language translation thereof (11 pages).

(Continued)

*Primary Examiner* — Kenneth M Lo
*Assistant Examiner* — David J Wynne
(74) *Attorney, Agent, or Firm* — Drinker Biddle & Reath LLP

(57) ABSTRACT

A method of manufacturing a surgical kit for cartilage repair in an articulating surface of a joint, comprising the steps of receiving radiology image data representing three dimensional image of a joint; generating a first three dimensional representation of a first surface of the joint in a trainable image segmentation process dependent on a trained segmentation process control parameter set and said radiology image data; generating a set of data representing a geometrical object based on said first surface, wherein said geometrical object is confined by said first surface; generating control software adapted to control a CAD or CAM system to manufacture a surgical kit for cartilage repair dependent on said set of data representing a geometrical object and on a predetermined model of components of said surgical kit.

13 Claims, 13 Drawing Sheets

(51) Int. Cl.
| | |
|---|---|
| *G05B 19/4097* | (2006.01) |
| *A61B 5/055* | (2006.01) |
| *A61B 6/03* | (2006.01) |
| *A61B 8/00* | (2006.01) |
| *G06T 7/12* | (2017.01) |
| *G06T 7/10* | (2017.01) |

(52) U.S. Cl.
CPC ............ *A61B 8/00* (2013.01); *A61F 2/30756* (2013.01); *A61F 2/30942* (2013.01); *G05B 19/4097* (2013.01); *G06T 7/10* (2017.01); *G06T 7/12* (2017.01); *A61B 2034/108* (2016.02); *A61F 2002/30948* (2013.01); *A61F 2002/30952* (2013.01); *A61F 2002/30953* (2013.01); *G05B 2219/32287* (2013.01); *G05B 2219/35012* (2013.01); *G06T 2207/10072* (2013.01); *G06T 2207/20081* (2013.01); *G06T 2207/30008* (2013.01)

(58) Field of Classification Search
CPC ........... A61B 2034/108; A61F 2/30756; A61F 2002/30952; A61F 2002/30948
See application file for complete search history.

(56) References Cited

U.S. PATENT DOCUMENTS

| | | | |
|---|---|---|---|
| 2002/0087274 A1 | 7/2002 | Alexander et al. | |
| 2009/0092301 A1* | 4/2009 | Jerebko | G06T 17/20 |
| | | | 382/128 |
| 2010/0303317 A1* | 12/2010 | Tsougarakis | A61F 2/30756 |
| | | | 382/128 |
| 2011/0087465 A1* | 4/2011 | Mahfouz | G06F 19/3437 |
| | | | 703/1 |
| 2012/0192401 A1* | 8/2012 | Pavlovskaia | G06F 19/00 |
| | | | 29/428 |
| 2013/0245801 A1 | 9/2013 | Schroeder | |

FOREIGN PATENT DOCUMENTS

| | | |
|---|---|---|
| JP | 2002-532126 A | 10/2002 |
| JP | 2012-518519 A | 8/2012 |
| JP | 2012-518520 A | 8/2012 |
| WO | WO-2004/043305 A1 | 5/2004 |
| WO | WO-2010/140036 A1 | 12/2010 |
| WO | WO-2012018851 A1 * 2/2012 ........... A61B 8/0875 |
| WO | WO-2013/020026 A1 | 2/2013 |

OTHER PUBLICATIONS

Communication from the Examining Division dated Jun. 28, 2017 issued in corresponding European patent application No. 14 705 730.1 (6 pages).
Japanese Notification of Reasons for Refusal dated Oct. 30, 2017 issued in corresponding Japanese patent application No. 2016-546813 (3 pages) and its English-language translation thereof (4 pages).
Josephson, Klas, et al., "Segmentation of Medical Images Using Three-Dimensional Active Shape Models," SCIA 2005, LNCS 3540 (2005), pp. 719-728.
Cootes, T.F., et al., "Statistical Models of Appearance for Computer Vision," Imaging Science and Biomedical Engineering, University of Manchester, Mar. 8, 2004, pp. 1-125, http://www.isbe.man.ac.uk.
Heimann, Tobias, et al., "Statistical shape models for 3D medical image segmentation: A review," Medical Image Analysis, vol. 13 (2009), pp. 543-563.
Extended European Search Report dated Aug. 31, 2018, that issued in EP Patent Application No. 18173418.7-1210.

* cited by examiner

METHOD AND NODE FOR MANUFACTURING A SURGICAL KIT FOR CARTILAGE REPAIR

RELATED APPLICATION DATA

This application is a continuation application of pending prior U.S. patent application Ser. No. 15/116,829, filed Aug. 5, 2016, which is the National Stage of International Application No. PCT/EP2014/052417 filed Feb. 7, 2014, which are all herein incorporated in their entirety.

TECHNICAL FIELD

Generally, embodiments of the invention relate to the technical field of designing and manufacturing customized implants used for patient treatment in health care based on radiology imaging.

More specifically, different embodiments of the application relate to a process and a system for manufacturing a surgical kit for cartilage repair in an articulating surface of a joint.

BACKGROUND

Radiology is a medical technique that uses imaging to diagnose and treat patients for health related issues. An array of imaging techniques are used in radiology, like X-ray radiography, ultrasound, computed tomography (CT), nuclear medicine, positron emission tomography (PET) and magnetic resonance imaging (MRI).

The patient is exposed to radiology imaging technology by capturing three dimensional radiology images, e.g. of a knee joint, that can provide information about the human body's internal structures. This occurs in a medical care facility, e.g. at a radiology department of a hospital. The images and the information obtained are forwarded to an implant design center for design of an implant and resulting control software (CAD/CAM), e.g. to improve or repair damaged cartilage, e.g. in a damaged human knee.

In conventional systems implants may be manufactured as surgical kits in standard sizes and might be supplied with standard guides to support in implant surgery, e.g. to support in determining the position and mounting angle of the implant.

A problem with conventional systems is that implants are poorly customized to patients that may lead to replacement of unnecessary large areas of undamaged cartilage bad alignment of the top surface of the implant to the cartilage top surface being replaced, which in turn might lead to reduced or no improvement of the condition of the person being subjected to implant surgery.

Another problem is that three dimensional representations of surfaces in the body, e.g. a 3D surface derived from a radiology 3D image of an articulating surface of a joint, that are generated based on three dimensional radiology images are generally not as smooth as the surface of healthy cartilage tissue.

Yet another problem is to generate or derive an accurate three-dimensional representation of a surface of a joint based on 3D radiology images and a segmentation process, wherein the segmentation process is controlled by a segmentation process control parameter set.

Yet another problem is to estimate an undamaged cartilage top surface in an area with damaged cartilage top surface by obtain a segmentation process control parameter set that will enable improved manufacturing of a patient customized surgical kit for cartilage repair.

Therefore, there is a need for a system and method to improve manufacturing of a surgical kit for cartilage repair.

Object of the Invention

The object of the invention is to improve manufacturing of a patient customized surgical kit for cartilage repair.

SUMMARY

Embodiments of the present invention relate to improved manufacturing of a surgical kit for cartilage repair. Certain embodiments include receiving radiology image data representing three dimensional image of a joint, generating a first three dimensional representation of a first surface of the joint in a trainable image segmentation process dependent on a trained segmentation process control parameter set and said radiology image data, generating a second three dimensional representation of a second surface of the joint in a trainable dynamical model process dependent on a trained dynamical model process control parameter set and said radiology image data, generating a cartilage damage perimeter CDP based on said radiology image data, generating a set of data representing a geometrical object based on said first surface, said second surface and said CDP, wherein said geometrical object represent identified cartilage damage, wherein said geometrical object is confined by said first surface, said second surface and said CDP and generating control software adapted to control a CAD or CAM system to manufacture a surgical kit for cartilage repair dependent on said set of data representing a geometrical object and on a predetermined model of components of said surgical kit.

One of the advantages of the present disclosure is that improved customization of a cartilage implant to a patient's body is achieved.

Another advantage of the present disclosure is that a smooth surface aligning well with remaining healthy cartilage tissue is obtained after implant surgery.

Another advantage of the present disclosure is that an accurate three-dimensional representation of a surface of a joint is obtained.

Another advantage of the current disclosure is that an improved segmentation process control parameter set is obtained, thereby enabling improved manufacturing of a patient customized surgical kit for cartilage repair.

In one or more embodiments, a method of manufacturing a surgical kit for cartilage repair in an articulating surface of a joint, comprising the steps of:
  receiving radiology image data representing three dimensional image of a joint;
  generating a first three dimensional representation (330, 460) of a first surface of the joint (260) in a trainable image segmentation process dependent on a trained segmentation process control parameter set (420) and said radiology image data;
  generating a set of data representing a geometrical object based on said first surface, wherein said geometrical object is confined by said first surface;
  generating control software adapted to control a CAD or CAM system to manufacture a surgical kit for cartilage repair dependent on said set of data representing a geometrical object and on a predetermined model of components of said surgical kit.

In one or more embodiments, further comprising the step generating a second three dimensional representation (320)

of a second surface of the joint (230) in a trainable dynamical model process dependent on a trained dynamical model process control parameter set and said radiology image data; and;

generating a set of data representing a geometrical object further based on said second three dimensional representation, wherein said geometrical object is further confined by said second surface;

In one or more embodiments, further comprising the step generating a cartilage damage perimeter CDP based on said radiology image data; and;

generating a set of data representing a geometrical object further based on said CDP, wherein said geometrical object is further confined by said CDP;

In one or more embodiments, further comprising the step generating a surgical kit perimeter SKP based on said radiology image data; and;

generating a set of data representing a geometrical object further based on said SKP, wherein said geometrical object is further confined by said SKP;

In one or more embodiments, wherein generating a first three-dimensional representation of a first surface of the joint in a trainable image segmentation process further comprises the steps:

I) obtaining a predefined ordered set of segmentation process control parameters instances;

II) generating a first three dimensional representation of said first surface based on the first instance of said trained segmentation process control parameter set and said radiology image data;

III) store said first three-dimensional representation in a data buffer

IV) generating a first three dimensional representation 460 of said first surface based on the next instance of said trained segmentation process control parameter set and said radiology image data;

V) store said first three-dimensional representation in a data buffer

VI) repeating steps IV and V for all instances of said predefined ordered set;

VII) determining an updated trained segmentation process control parameter set based on a first three dimensional representation quality value, wherein said first three dimensional representation quality value is based on said three dimensional representations stored in the data buffer, said predefined ordered set and a predetermined object function.

In one or more embodiments, wherein generating a first three dimensional representation of a first surface of the joint in a trainable image segmentation process further comprises the steps:

XI) obtaining an initial segmentation process control parameter set;

XII) determining a trained segmentation process control parameter set as said initial segmentation process control parameter set;

XIII) generating a first three dimensional representation of said first surface based on said trained segmentation process control parameter set and said radiology image data;

XIV) determining a differential trained segmentation process control parameter set based on a first three dimensional representation quality value, wherein said first three dimensional representation quality value is based on said three dimensional representation and a predetermined object function.

XV) determining an updated trained segmentation process control parameter set based on said trained segmentation process control parameter set and said differential trained segmentation process control parameter set XVI) repeating steps XIII-XVI above if said first three dimensional representation quality value is below or above a predefined quality value threshold.

In one or more embodiments, wherein generating a second three dimensional representation of a second surface of the joint in a trainable image segmentation process further comprises the steps:

XX) obtaining an initial dynamical model process control parameter set;

XXI) determining a trained dynamical model process control parameter set as said initial dynamical model process control parameter set;

XXII) generating a second three dimensional representation of said second surface based on said trained dynamical model process control parameter set and said radiology image data;

XXIII) determining a differential trained dynamical model process control parameter set based on a three-dimensional representation quality value, wherein said three dimensional representation quality value is based on said three-dimensional representation.

XXIV) determining an updated trained dynamical model process control parameter set based on said trained dynamical model process control parameter set and said differential trained dynamical model process control parameter set;

XXV) repeating steps XX-XXV above if said three dimensional representation quality value is below or above a predefined quality value threshold.

In one or more embodiments, wherein said radiology image data is based on a selection of X-ray, ultrasound, computed tomography (CT), nuclear medicine, positron emission tomography (PET) and magnetic resonance imaging (MRI).

In one or more embodiments, an implant design center system for manufacturing a surgical kit for cartilage repair in an articulating surface of a joint, the system comprising:
    a memory 830;
    a communications interface 840;
    a processor 810 configured to perform the steps of:
    receiving radiology image data representing three dimensional image of a joint;
    generating a first three dimensional representation of a first surface of the joint in a trainable image segmentation process dependent on a trained segmentation process control parameter set and said radiology image data;
    generating a set of data representing a geometrical object based on said first surface, wherein said geometrical object is confined by said first surface;
    generating control software adapted to control a CAD or CAM system to manufacture a surgical kit for cartilage repair dependent on said set of data representing a geometrical object and on a predetermined model of components of said surgical kit.

A computer program product comprising computer readable code configured to, when executed in a processor, perform any or all of the method steps described herein.

A non-transitory computer readable memory on which is stored computer readable code configured to, when executed in a processor, perform any or all of the method steps described herein.

BRIEF DESCRIPTION OF DRAWINGS

Embodiments of the invention will now be described in more detail with reference to the appended drawings, wherein.

DETAILED DESCRIPTION

Introduction

Figure 1A:
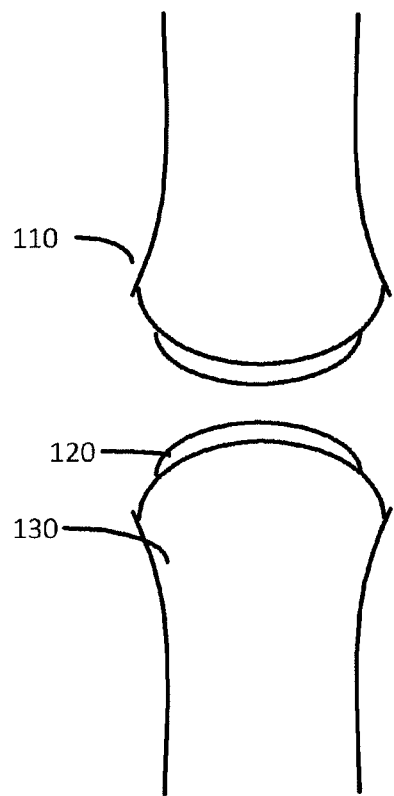
FIG. 1a illustrates healthy joint with bone and cartilage tissue.

When repairing cartilage by performing cartilage implant surgery, a first problem is to determine the design or dimensions of an implant. The implant is generally linked or attached to a patient's body by inserting an implant support into a drilled cavity, e.g. into the bone. Therefore yet another problem is to ensure that the cartilage implant is placed and located correctly, i.e. that the position and mounting angle of the implant is correct, thereby aligning the outer or top surface of the implant to the remaining cartilage tissue.

The inventive concept described herein solves this by providing an implant and a matching implant guide, referred to as a surgical kit, based on radiology image data. The implant guide may be positioned and attached to the patient's body, typically the bone to which the cartilage is attached, thereby allowing a cavity to be drilled in the correct location and mounting angle for insertion of the implant support.

To customize the surgical kit to a particular patient the design of the surgical kit is obtained by adapting a model of components, comprising an implant component and an implant guide component. The outline of the implant is determined based on a cartilage damage perimeter (CDP), indicating the extent of the cartilage damage, e.g. on a second surface of the joint. The outline of the implant guide is determined by generating a surgical kit perimeter (SKP), indicating the area on a first surface of the joint, such as the underlying bone, available on a particular patient to place an implant guide in. The outer or top surface of the implant is determined by the remaining cartilage tissue outer surface and adapted so that a smooth transition between the cartilage outer surface and the implant outer surface is obtained, i.e. aligned to remaining cartilage tissue outer surface. The model of components is then adapted based on the first surface of the joint and alternatively the second surface of the joint, CDP and SKP.

To adapt the model components a first three dimensional representation of a first surface of the joint and optionally a second three dimensional representation of a second surface of the joint, CDP and optionally SKP are generated based on radiology image data.

To extract the first surface from radiology image data, a first three-dimensional representation of a first surface may be generated by in an image segmentation process dependent on a segmentation process control parameter set.

The outer or top surface of the implant is replacing damage tissue. The outer or top surface of damaged tissue will not be identifiable in the radiology image data, however the undamaged tissue may be identified and used to adapt a dynamical model of a second surface to align with the undamaged tissue. Therefore, a second three dimensional representation of a second surface of the joint may be generated in a dynamical model process dependent on a dynamical model process control parameter set.

Once the first three dimensional representation and optionally the second three dimensional representation, said CDP and said SKP have been generated, a set of data representing a geometrical object may be generated and used to generate control software adapted to control a CAD or CAM system to manufacture a surgical kit for cartilage repair.

Definitions

Surgical kit for cartilage repair is in this text to be understood as a customized pair of implant and implant guide adapted to a person or patient, scheduled for implant surgery, wherein the implant guide is configured to relieve and support the surgeon in implant surgery by guiding the implant to the wanted position and with the correct mounting angle on a person being subjected to implant surgery. If the implant is offset from its intended position it may cause an increased wear or load on the joint. A difficult task of a surgeon is to place or locate an implant. There is therefore a need for well-fitting implants as well as tools that are designed to relieve and support the surgeon in implant surgery. The design of the implant and the guide, in other words the design of the surgical kit, is crucial for the outcome of the implants lifetime in a patients joint. Small differences in the placement or design of the implant can make a huge difference in the benefit and lifetime of an implant in the patient's body, convalescence time for the patient, economic values due to surgery time, success rate of implant surgery.

Surface of a joint is in this text to be understood as a surface associated to cartilage, such as the inner surface of the cartilage connected to the bone or the outer surface of the cartilage.

Radiology image data representing a three dimensional image of a joint is in this text to be understood as data arranged in a three dimensional array of voxels or pixels or multiple ordered two dimensional images obtained at a predefined distance. The pixels may comprise pixel values of a predetermined resolution, e.g. 8, 16 or 32 bits, wherein the pixel values may indicate an intensity or greyscale value. In one example, radiology image data is in the form of a 3D array of voxels or pixels. Each voxel may have an intensity or greyscale value, e.g. in the range from 0 to 65535 in the 16-bit pixel case or 0 to 255 in the 8-bit pixel case. Most medical imaging systems generate images using 16-bit greyscale range. A 3D image typically has a large number of pixels and is very computational intensive for processing such as segmentation and pattern recognition. To reduce complexity and computational intensity three-dimensional representations of a first surface may be generated, e.g. in a process called segmentation.

Three-dimensional representation is in this text to be understood as data values arranged in a data structure, such as an array, representing a three dimensional (3D) surface. Such a 3D surface may be a selection of voxels from a 3D radiology image data, a three-dimensional mesh, a parametric surface, a surface model or any other representation of a 3D surface known to a person skilled in the art.

Trainable process is in this text to be understood as a process with associated input data, such as image data, geometrical model and control parameters, and output data, such as a three dimensional representation, adapted with a training unit configured to evaluate the output data by generating a quality value and modifying the input data based on the quality value in order to iterate the process. The iterations may continue until the quality value exceeds a predefined threshold value.

Image segmentation process is in this text to be understood as a process configured to partition image data in a semantically meaningful way to generate a three dimensional representation, e.g. identifying an articulating surface of a joint such as an inner surface of the cartilage connected to the bone, based on dynamical segmentation process control parameters and radiology image data.

Segmentation process control parameter set is in this text to be understood as control parameters controlling the image segmentation process and therefore the properties of a three dimensional representation generated by the image segmentation process. Examples of such parameters may be Desired hole radius, Number of classes to identify as different regions or tissue types, Error tolerance for clustering, grayscale values into different classes, Degree of smoothness on the classified regions, Number of iterations, down sample factor or Spline distance.

Dynamical model process is in this text to be understood as a process configured to adapt a dynamical model of a surface to align with predetermined features of radiology image data, such as undamaged cartilage tissue along a perimeter or an estimated surface of undamaged cartilage, to generate a second three dimensional representation based on dynamical model process control parameters and radiology image data.

Dynamical model process control parameter set is in this text to be understood as control parameters controlling the dynamical model process and thereby properties of the generated three-dimensional representation.

Perimeter is in this text to be understood as a perimeter delimiting a subset of a three dimensional representation.

Cartilage damage perimeter (CDP) is in this text to be understood as a perimeter delimiting a subset of a first or second three dimensional representation. In one example, this may comprise identifying the perimeter of an implant, part of a surgical kit, to be manufactured.

Surgical kit perimeter (SKP) is in this text to be understood as a perimeter delimiting a subset of a first three dimensional representation. In one example, this may comprise identifying the perimeter of possible locations of a guide, part of a surgical kit, to be manufactured.

Geometrical object is in this text to be understood as a geometrical object or volume delimited by a subset of the first three dimensional representation as the bottom, a subset of second three dimensional representation as the top and a surface interconnecting said top of the geometrical object and said bottom of the geometrical object. The subset of the first or second three-dimensional representation may be delimited by a perimeter, such as the CDP or a surgical kit perimeter SKP.

Control software adapted to control a CAD or CAM system is in this text to be understood as data values represented by data structures comprising computer program code portions configured to direct a processor to perform display or manufacturing of a surgical kit for cartilage repair in an articulating surface of a joint Predetermined model of components is in this text to be understood as a model comprising an implant component and an implant guide component that may be adapted based on a geometrical object, radiology image data, a first three dimensional representation and a second three dimensional representation. In one example, the implant component is adapted in size to replace damaged cartilage and the implant guide component is adapted to fit on the first and second three-dimensional representation, to enable fixation points to the first surface or bone, to enable correct positioning of the implant component and to enable the correct mounting angle for the implant component.

Three dimensional representation quality value is in this text to be understood as a quality value determined on a predetermined relation based on a three dimensional representation. In one example, this might involve comparing three-dimensional representation to a reference surface, e.g. by generating a measure of distances between the surfaces in Euclidian space. In yet another example this might involve evaluating the smoothness of a three dimensional representation or the deviation of a three dimensional representation compared to a reference surface.

Drawings Descriptions

FIG. 1a illustrates healthy joint 110 with bone 130 and cartilage tissue 120.

Figure 1B:
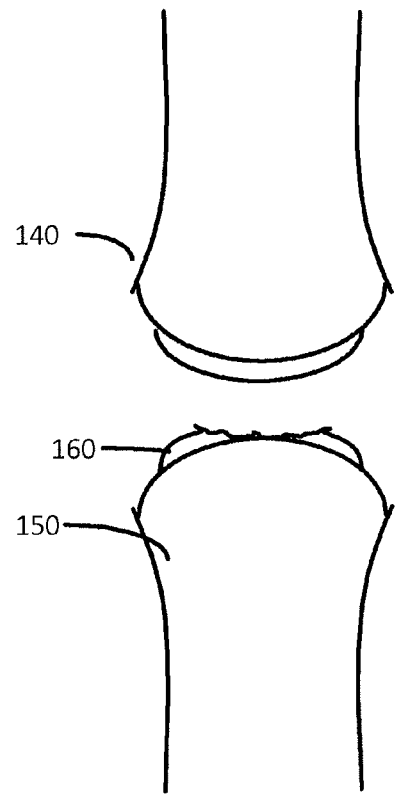
FIG. 1b illustrates a damaged joint with bone and damaged cartilage tissue.

FIG. 1b illustrates a damaged joint 140 with bone 150 and damaged cartilage tissue 160.

Figure 2A:
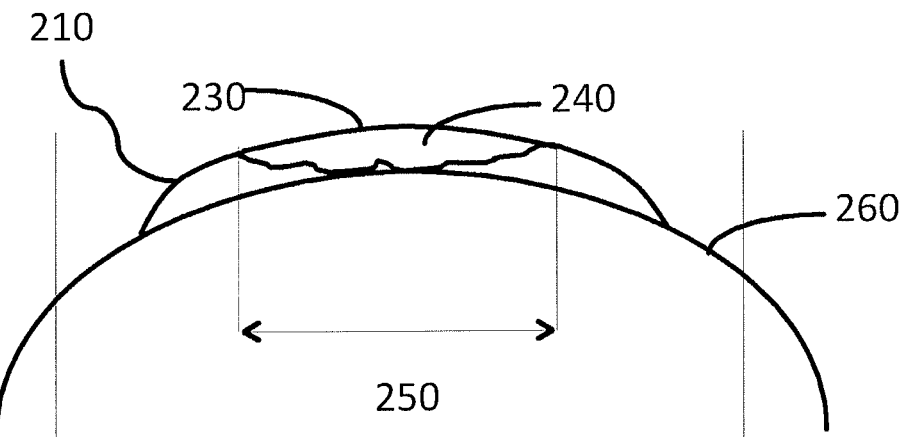
FIG. 2a illustrates a side view intersection of a generated first three-dimensional representation of a first surface of the joint, a generated second three-dimensional representation of a second surface of the joint, a generated cartilage damage perimeter CDP and a generated surgical kit perimeter SKP in accordance with one or more embodiments of the present disclosure.

FIG. 2a illustrates a side view intersection of a generated first three dimensional representation of a first surface 260 of the joint, a generated second three dimensional representation of a second surface of the joint 230, a generated cartilage damage perimeter CDP 250 and a generated surgical kit perimeter SKP 270 in accordance with one or more embodiments of the present disclosure. FIG. 2a further illustrates how said second three-dimensional representation of a second surface of the joint 230 is aligned to remaining cartilage tissue outer surface.

Figure 2B:
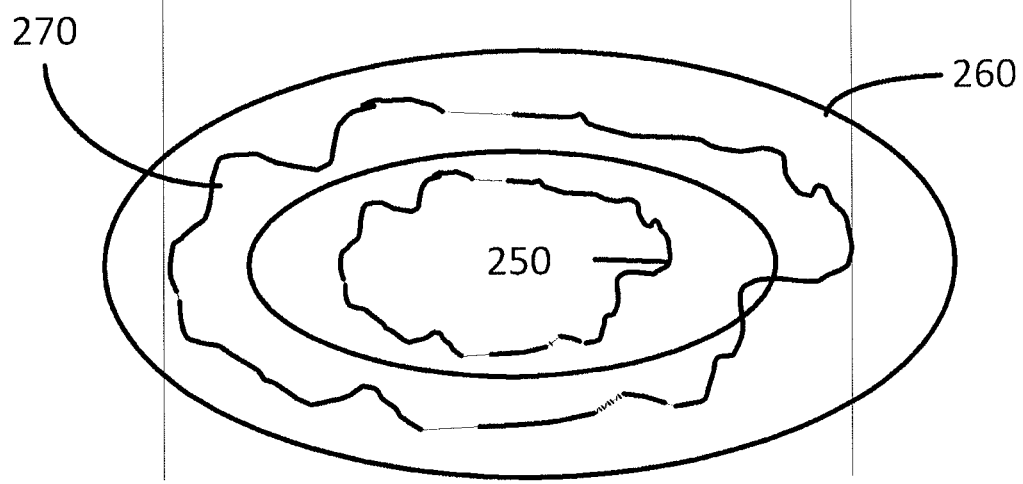
FIG. 2b illustrates a top view of a generated first three-dimensional representation of a first surface of the joint, a generated second three-dimensional representation of a second surface of the joint, a generated cartilage damage perimeter CDP and a generated surgical kit perimeter SKP in accordance with one or more embodiments of the present disclosure.

FIG. 2b illustrates a top view of a generated first three dimensional representation of a first surface of the joint 260, a generated cartilage damage perimeter CDP 250 and a generated surgical kit perimeter SKP 270 in accordance with one or more embodiments of the present disclosure.

Figure 3A:
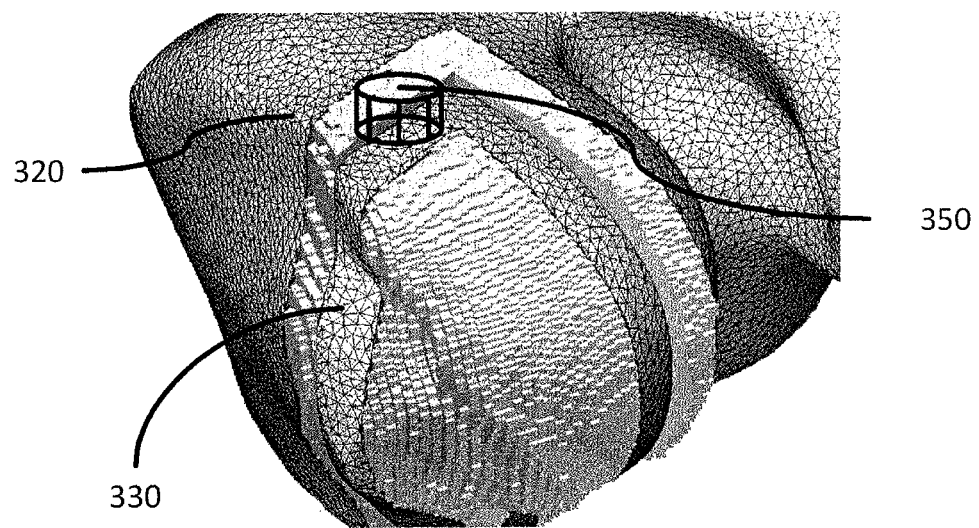
FIG. 3a shows a schematic view of an embodiment of a first three dimensional representation of a first surface of the joint, a second three dimensional representation of a second surface of the joint and a geometrical object.

FIG. 3a shows a schematic view of an embodiment of a generated first three-dimensional representation 330 of a first surface of the joint, a generated second three-dimensional representation 320 of a second surface of the joint and a geometrical object 350. In one or more embodiments the geometrical object is generated based on the CDP, the first three dimensional representation and the second three dimensional representation. In one or more embodiments said first three-dimensional representation 330 is represented in the form of selected voxels in the radiology image data, a polygon mesh, an anatomical model or a parametric surface.

In one non-limiting example an implant mounting position is determined as a position on the first three dimensional representation comprised by CDP and an implant mounting angle is determined as the normal or surface normal vector of the first three dimensional representation. A first subset of said first three-dimensional representation is determined based on the CDP. The CDP is further translated along an axis represented by the implant mounting angle to the second three dimensional representation and second subset of said first three dimensional representation is determined based on the translated CDP. A geometric object is then generated based on the first subset, the second subset and a surface interconnecting said first subset and second subset.

Figure 3B:
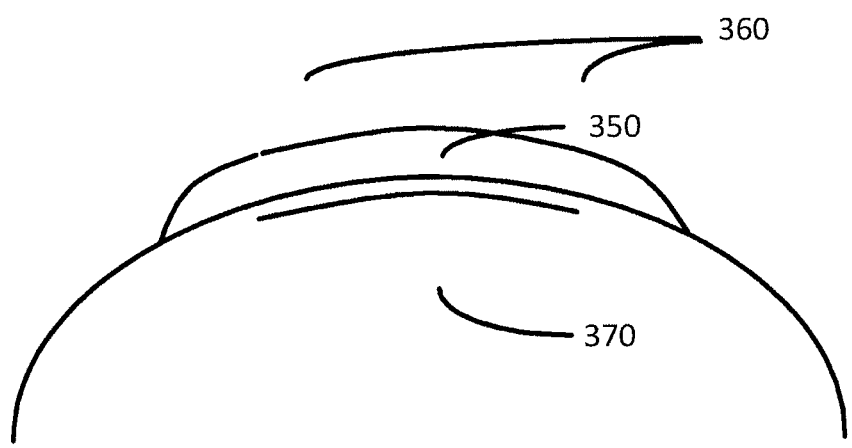
FIG. 3b shows a schematic view of an embodiment of an adapted implant component comprised in a model of components of a surgical kit based on a geometrical object and an adapted implant guide component comprised in a model of components of a surgical kit based on a geometrical object.

FIG. 3b illustrates a surgical kit manufactured based on control software adapted to control a CAD or CAM system to manufacture a surgical kit for cartilage repair dependent on a set of data representing a geometrical object and on a predetermined model of components of said surgical kit according to the method of the present disclosure. In one or more embodiments, the predetermined model of components comprises an implant component 350 and an implant guide component 360. In one or more embodiments, the predetermined model of components further comprises an implant support component 370. In one or more embodiments, the implant component is adapted based on the geometrical object. In one or more embodiments, the implant guide component is adapted based on the geometrical object and SKP.

In one non-limiting example, the implant component is adapted by scaling and rotating the implant component so that it is comprised in said geometrical object and so that the top or outer surface of the implant component is aligned with the geometrical object, thereby also aligning with the undamaged cartilage tissue.

To design and manufacture a customized surgical kit for cartilage repair in an articulating surface of a joint it is necessary to identify a reference surface, such as the bone underlying the cartilage tissue. This reference surface is identified by extracting a first surface from radiology image data, e.g. by generating a first three dimensional representation of a first surface in a radiology image segmentation process dependent on a segmentation process control parameter set. The quality and accuracy of this generated first three-dimensional representation or surface depend on the segmentation process control parameter set and may vary for the individual patient and for individual types of joints, e.g. knee, toe, elbow etc. To further quality and accuracy of this generated first three-dimensional representation, the segmentation process control parameter set may be obtained through parameter training. Parameter training generally comprise attempting to fit a certain model, e.g. an objective function, to observed data such as a first three dimensional representation of a first surface.

Figure 4:
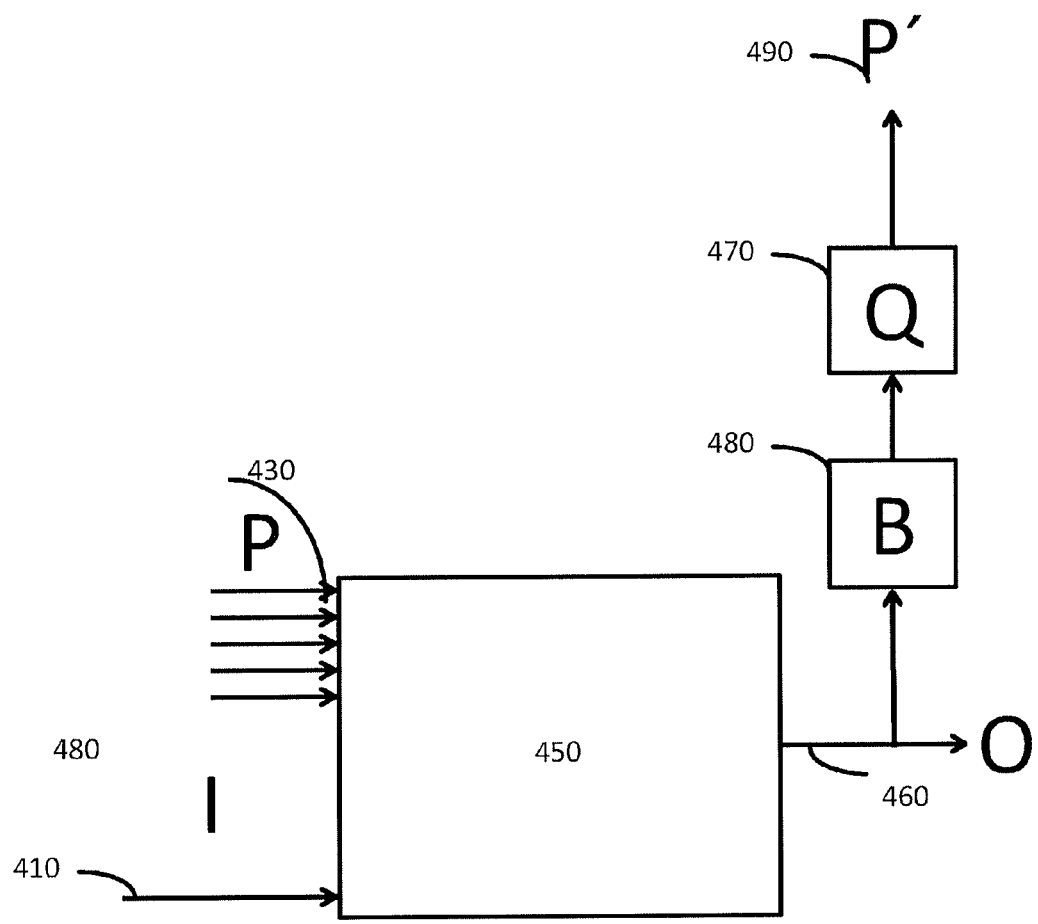
FIG. 4 shows a schematic view of an embodiment of a trainable image segmentation process.

FIG. 4 shows a schematic view of an embodiment of a method for a trainable image segmentation process according to the present disclosure. In one or more embodiment a first three dimensional representation 460 of a first surface of the joint is generated in a trainable image segmentation process 450 dependent on a trained segmentation process control parameter set 430 and radiology image data 410. In one or more embodiments, the method further comprises:

I) obtaining a predefined ordered set of segmentation process control parameters instances;

II) generating a first three dimensional representation 460 of said first surface based on the first instance of said trained segmentation process control parameter set and said radiology image data;

III) store said first three-dimensional representation in a memory or data buffer 480;

IV) generating a first three dimensional representation 460 of said first surface based on the next instance of said trained segmentation process control parameter set and said radiology image data;

V) store said first three-dimensional representation in a data buffer 480;

III) repeating steps I and II for all instances of said predefined ordered set;

IV) determining an updated trained segmentation process control parameter set 490 based on a first three dimensional representation quality value, wherein said first three dimensional representation quality value is based on said three dimensional representations stored in the data buffer 480, said predefined ordered set and a predetermined object function.

In one non-limiting example, a predefined number of instances of segmentation process control parameters are obtained as an ordered set, e.g. ten previously used parameter sets used in a segmentation process. A first three dimensional representation is generated for each instance of segmentation process control parameters and stored in a data buffer or memory. An object function, e.g. a measure of how a segmented surface deviate from a reference surface such as a parametric surface, is used to determine a first three-dimensional representation quality value. An updated trained segmentation process control parameter set is then determined, e.g. by selecting an instance from the ordered set based on the first three dimensional representation quality value, by combining instances from the ordered set based on the first three dimensional representation quality value or to generate a new instance of a trained segmentation process control parameter set. In alternative embodiments, any objective function known to the skilled person may be used, such as roughness Measures for 3D surfaces/meshes.

Figure 5:
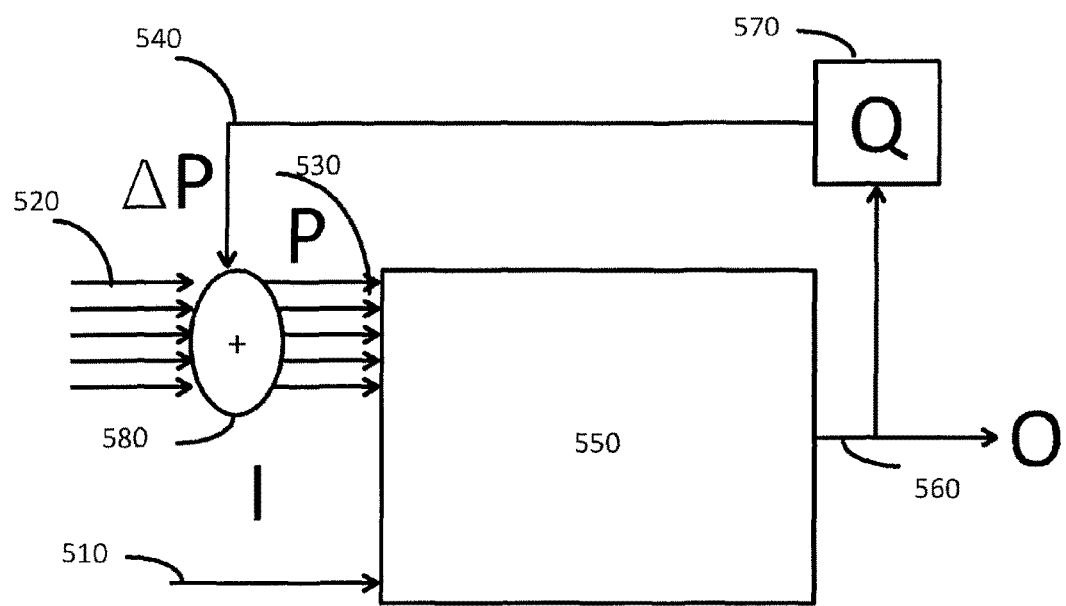
FIG. 5 shows a schematic view of an alternative embodiment of a trainable image segmentation process.

FIG. 5 shows a schematic view of an embodiment of a trainable image segmentation process according to method of the present disclosure. In one or more embodiment a first three dimensional representation 560 of a first surface of the joint in a trainable image segmentation process 550 dependent on a trained segmentation process control parameter set 530 and radiology image data 510. In one or more embodiments, the method further comprises:

I) obtaining an initial segmentation process control parameter set 520;

II) determining a trained segmentation process control parameter set 530 as said initial segmentation process control parameter set 520;

III) generating a first three dimensional representation 560 of said first surface based on said trained segmentation process control parameter set and said radiology image data;

IV) determining 570 a differential trained segmentation process control parameter set 540 based on a first three dimensional representation quality value, wherein said first three dimensional representation quality value is based on said three dimensional representation 560 and a predetermined object function.

V) determining an updated trained segmentation process control parameter set 530 based on said trained segmentation process control parameter set 520 and said differential trained segmentation process control parameter set 540

VI) repeating steps III-VI above if said first three dimensional representation quality value is below or above a predefined quality value threshold.

In one non-limiting example, an initial segmentation process control parameter set is obtained, e.g. as previously used and stored segmentation process control parameter set. The initial segmentation process control parameter set is determined as a trained segmentation process control parameter set and used together with received radiology image data, descriptive of a joint, in a trained segmentation process to generate a first three dimensional representation. The generated first three-dimensional representation is evaluated by a predetermined object function, e.g. a measure of how a segmented surface deviate from a reference surface, to obtain a first three-dimensional representation quality value. A differential trained segmentation process control parameter set is determined based on a first three dimensional representation quality value, e.g. by applying predetermined delta values to said trained segmentation process control parameter set or by performing a lookup in a predetermined table comprising trained segmentation process control parameter sets and first three dimensional representation quality values. An updated trained segmentation process control parameter set is further determined based on said differential trained segmentation process control parameter set and said trained segmentation process control parameter set. The method steps may then be repeated until it is determined that said first three-dimensional representation quality value is below, above or equal to a predefined quality value threshold.

Figure 6:
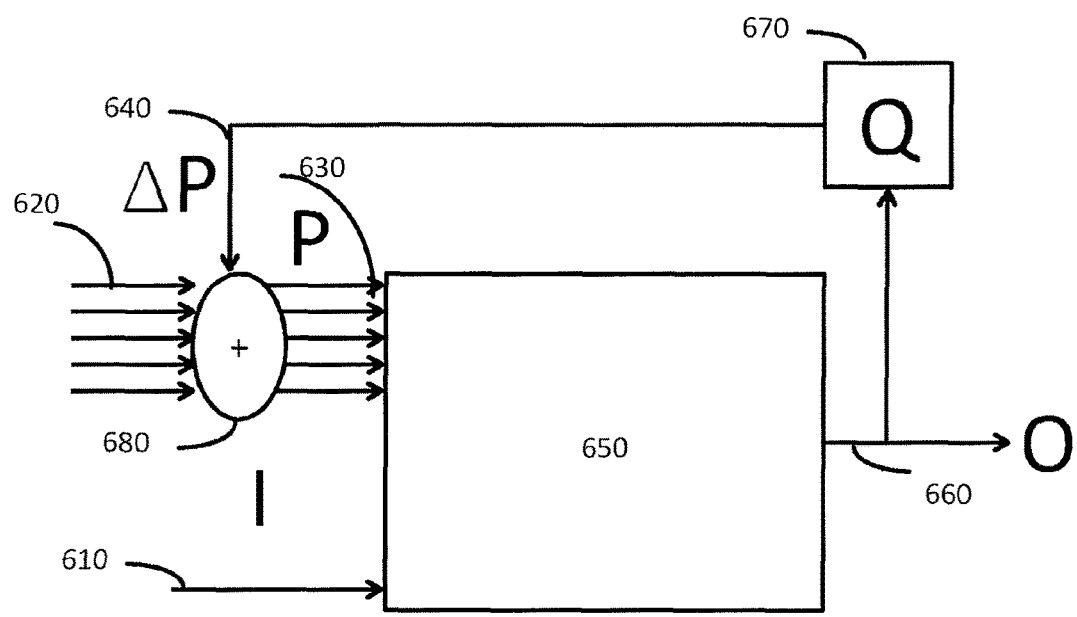
FIG. 6 shows a schematic view of an embodiment of a trained dynamical model process.

FIG. 6 shows a schematic view of an embodiment of a trainable dynamical model process according to method of the present disclosure. In one or more embodiments a second three dimensional representation 660 of a second surface of the joint in a trainable dynamical model process 650 dependent on a trained dynamical model process control parameter set 630 and radiology image data 610. In one or more embodiments, the method further comprises:

X) obtaining an initial dynamical model process control parameter set 620;

XI) determining a trained dynamical model process control parameter set 630 as said initial dynamical model process control parameter set 620;

XII) generating a second three dimensional representation 660 of said second surface based on said trained dynamical model process control parameter set and said radiology image data 610;

XIII) determining 670 a differential trained dynamical model process control parameter set 640 based on a three-dimensional representation quality value, wherein said three dimensional representation quality value is based on said three-dimensional representation 660.

XIV) determining an updated trained dynamical model process control parameter set 630 based on said trained dynamical model process control parameter set 620 and said differential trained dynamical model process control parameter set 640;

XV) repeating steps X-XV above if said three dimensional representation quality value is below or above a predefined quality value threshold.

In one or more embodiments, wherein generating a second three dimensional representation is further based on a dynamical model, such as an anatomical model or a parametric surface.

In one non-limiting example, an initial dynamical model process control parameter set is obtained, e.g. as the previously used and stored dynamical model process control parameter set. The initial dynamical model process control parameter set is determined as a trained dynamical model process control parameter set and used together with received radiology image data, descriptive of a joint, in a trained dynamical model process to generate a second three dimensional representation. The generated second three-dimensional representation is evaluated by a predetermined object function, e.g. a measure of how the generated second three-dimensional representation deviate from a reference surface, to obtain a second three-dimensional representation quality value. A differential trained dynamical model process control parameter set is determined based on a second three dimensional representation quality value, e.g. by applying predetermined delta values to said trained dynamical model process control parameter set or by performing a lookup in a predetermined table comprising trained dynamical model process control parameter sets and second three dimensional representation quality values. An updated trained dynamical model process control parameter set is further determined based on said differential trained dynamical model process control parameter set and said trained dynamical model process control parameter set. The method steps may then be repeated until it is determined that said second three-dimensional representation quality value is below, above or equal to a predefined quality value threshold.

Figure 7:
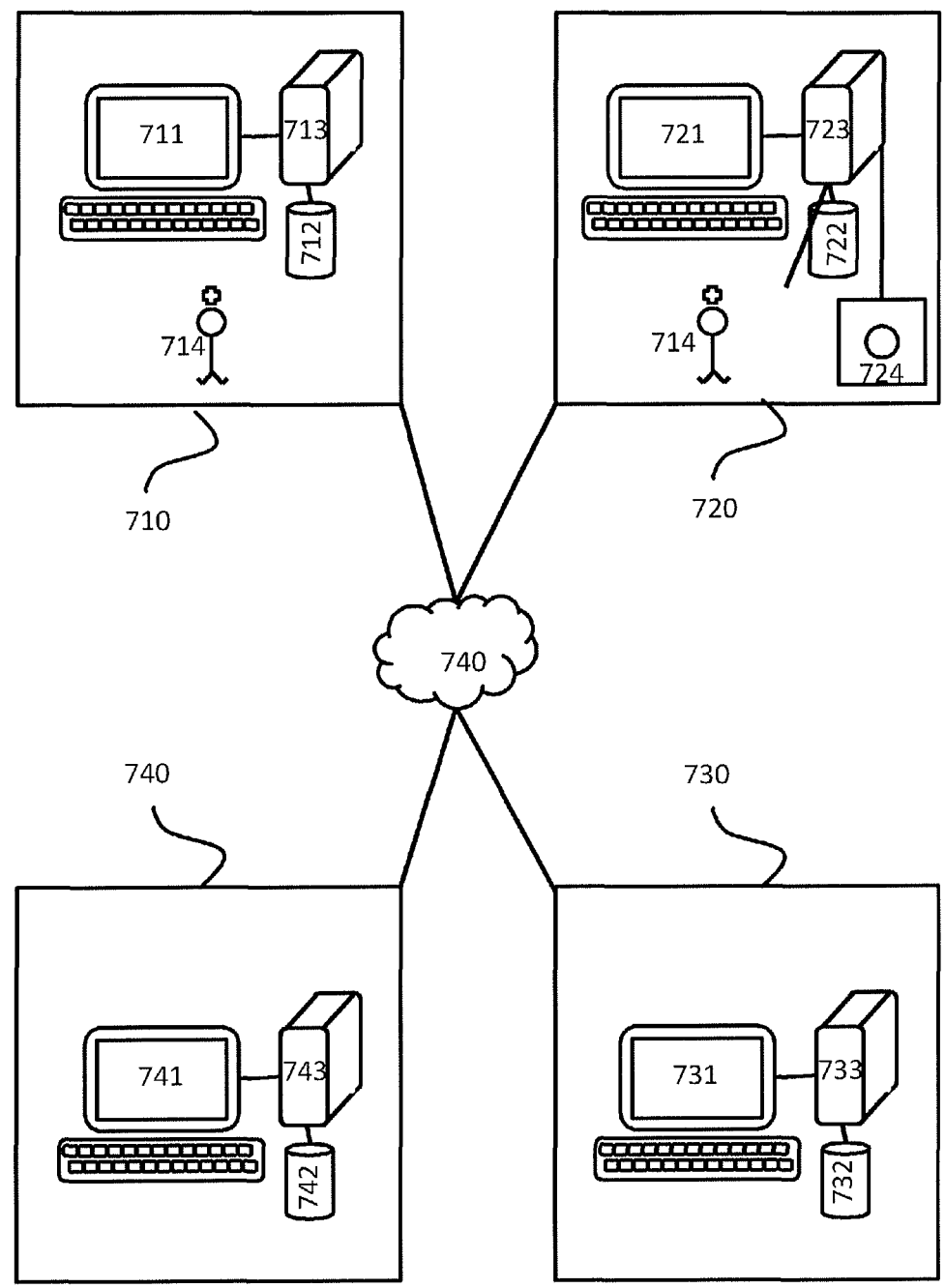
FIG. 7 shows a schematic view of an embodiment of a system for manufacturing a surgical kit for cartilage repair.

FIG. 7 shows a schematic view of an embodiment of a system for manufacturing a surgical kit for cartilage repair. In one or more embodiments the system comprises a diagnosis center 710 with a diagnosis processor 713 configured to accept user indications as diagnosis data indicative of cartilage damage and patient 714 related information via a user input/output device 711. The diagnosis processor 713 is further configured to send the diagnosis data via a communications network 740 to a radiology-imaging center 720. The radiology-imaging center 720 further comprises an imaging processor 723 configured to present diagnosis data to a user, to obtain radiology image data from a radiology image device 724, e.g. a CT or MR scanner, and to send diagnosis data and radiology image data as a signal via a communications network 740 to an implant design center. The implant design center comprises a processor 733 configured to receive diagnosis data and radiology image data and optionally store said diagnosis data and radiology image data to memory 732. The processor 733 is further configured to generating a first three dimensional representation of a first surface of the joint in a trainable image segmentation process dependent on a trained segmentation process control parameter set and said radiology image data, generating a second three dimensional representation of a second surface of the joint in a trainable dynamical model process dependent on a trained dynamical model process control parameter set and said radiology image data; generating a cartilage damage perimeter CDP based on said radiology image data, generating a set of data representing a geometrical object based on said first surface, said second surface and said CDP, wherein said geometrical object represent identified cartilage damage, wherein said geometrical object is confined by said first surface, said second surface and said CDP, generating control software adapted to control a CAD or CAM system to manufacture a surgical kit for cartilage repair dependent on said set of data representing a geometrical object and on a predetermined model of components of said surgical kit. The processor 733 is further configured to send said control software to an implant production center 740. The implant production center 740 comprises a processor 743 configured to receive control software and optionally store said diagnosis data and radiology image data to memory 742. The processor 743 is further configured to control a production line to manufacture a surgical kit for cartilage repair based on said received control software.

Figure 8:
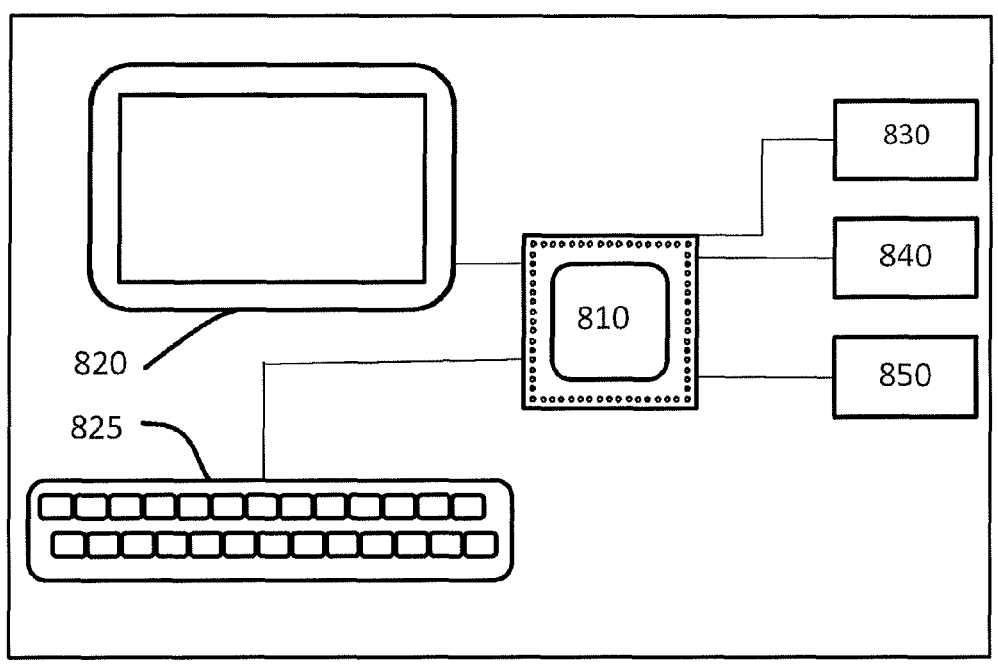
FIG. 8 shows a schematic view of an embodiment of an implant design center adapted to generate control software adapted to control a CAD or CAM system to manufacture a surgical kit for cartilage repair.

FIG. 8 shows a schematic view of an embodiment of an implant design center adapted to generate control software adapted to control a CAD or CAM system to manufacture a surgical kit for cartilage repair. In one or more embodiments, an implant design center, e.g. in the form of a tablet computer, laptop computer or desktop computer. Said implant design center is configured for generating control software adapted to control a CAD or CAM system to manufacture a surgical kit for cartilage repair. The design center further comprises a processor/processing unit 810 provided with specifically designed programming or program code portions adapted to control the processing unit 810 to perform the steps and functions of embodiments of the methods described herein. The computer system further comprises at least one memory 830 configured to store data values or parameters received from the processor 810 or to retrieve and send data values or parameters to the processor 810. In one or more embodiments, the design center further comprises a display configured to receive a signal from the processor 810 and to display the received signal as a displayed image, e.g. to a user of the design center. In one or more embodiments, the design center further comprises a user input device 825 configured to receive indications from a user and to generate data indicative of user input, thereby enabling the user to interact with the implant design center. The user input device 825 is further configured to send the generated data as a signal to said processor 810. In one or more embodiments computer system further comprises a communications interface 840 configured to send or receive data values or parameters to/from a processor 810 to/from external units via the communications interface 840. In one or more embodiments the communications interface 840 is configured to communicate via a communications network.

Further Embodiments

Figure 9:
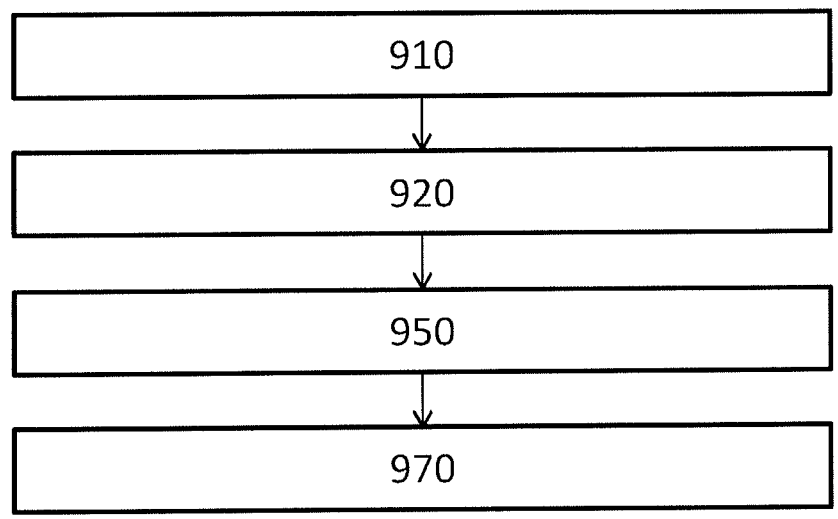
FIG. 9 shows a flowchart of an embodiment of a computer-implemented method to manufacturing a surgical kit.

FIG. 9 shows a flowchart of a computer-implemented method to manufacturing a surgical kit for cartilage repair in an articulating surface of a joint. In one or more embodiments, the method comprises the steps of:

receiving 910 radiology image data representing three-dimensional image of a joint;

generating 920 a first three dimensional representation of a first surface of the joint in a trainable image segmentation process dependent on a trained segmentation process control parameter set and said radiology image data;

generating 950 a set of data representing a geometrical object based on said first surface, wherein said geometrical object is confined by said first surface;

generating 970 control software adapted to control a CAD or CAM system to manufacture a surgical kit for cartilage repair dependent on said set of data representing a geometrical object and on a predetermined model of components of said surgical kit.

Figure 10:
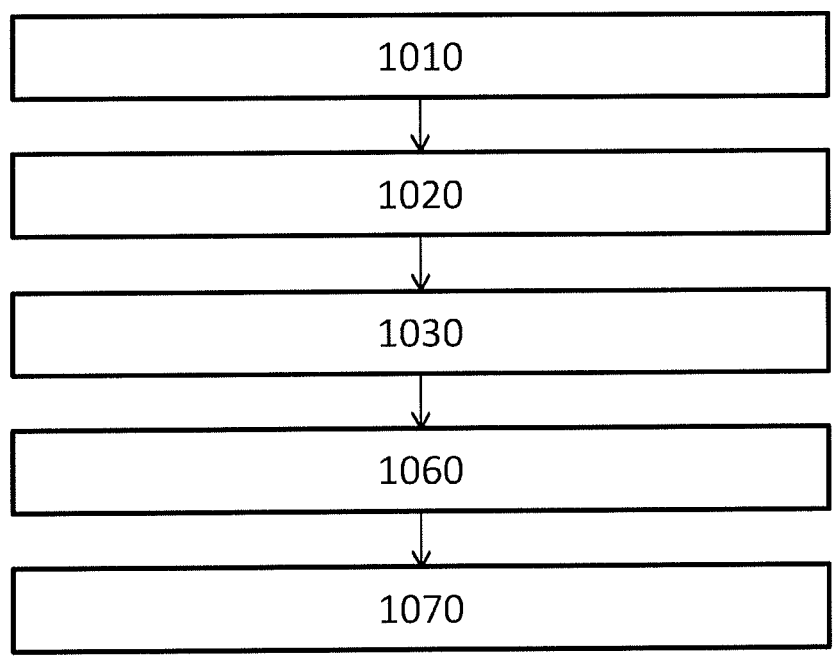
FIG. 10 shows a flowchart of yet an embodiment of a computer-implemented method to manufacturing a surgical kit for cartilage repair in an articulating surface of a joint.

FIG. 10 shows a flowchart of a computer-implemented method to manufacturing a surgical kit for cartilage repair in an articulating surface of a joint. In one or more embodiments, the method comprises the steps of:

receiving 1010 radiology image data representing three-dimensional image of a joint;

generating 1020 a first three dimensional representation of a first surface of the joint in a trainable image segmentation process dependent on a trained segmentation process control parameter set and said radiology image data;

generating 1030 a second three dimensional representation of a second surface of the joint in a trainable dynamical model process dependent on a trained dynamical model process control parameter set and said radiology image data;

generating 1060 a set of data representing a geometrical object based on said first surface, and said second surface, wherein said geometrical object is confined by said first surface and said second;

generating 1070 control software adapted to control a CAD or CAM system to manufacture a surgical kit for cartilage repair dependent on said set of data representing a geometrical object and on a predetermined model of components of said surgical kit.

Figure 11:
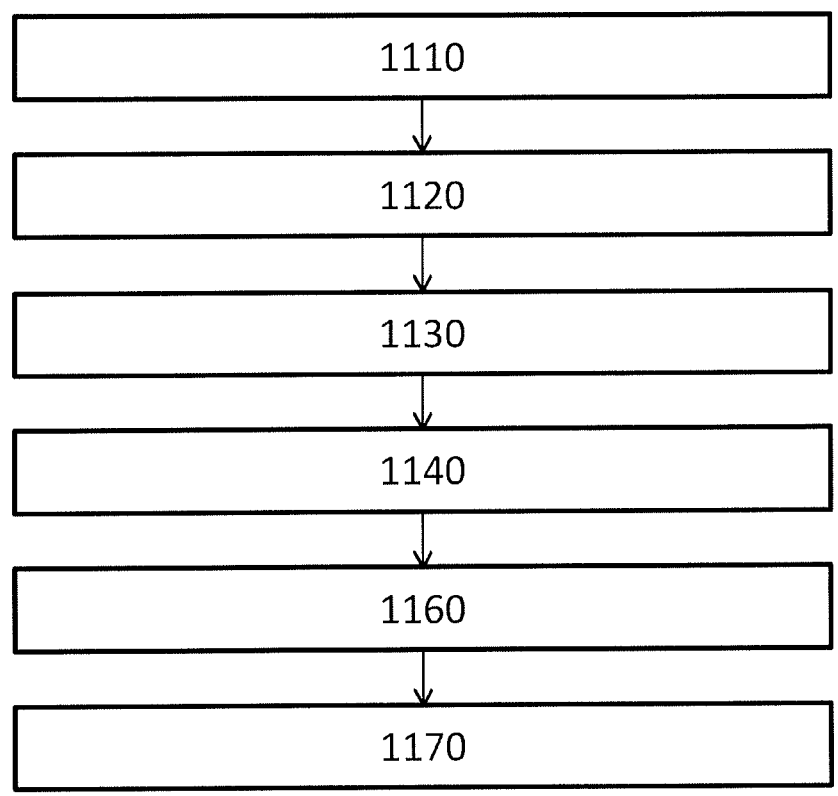
FIG. 11 shows a flowchart of yet an embodiment of a computer-implemented method to manufacturing a surgical kit for cartilage repair in an articulating surface of a joint.

FIG. 11 shows a flowchart of a computer-implemented method to manufacturing a surgical kit for cartilage repair in an articulating surface of a joint. In one or more embodiments, the method comprises the steps of: receiving 1110 radiology image data representing three-dimensional image of a joint;

generating 1120 a first three dimensional representation of a first surface of the joint in a trainable image segmentation process dependent on a trained segmentation process control parameter set and said radiology image data;

generating 1130 a second three dimensional representation of a second surface of the joint in a trainable dynamical model process dependent on a trained dynamical model process control parameter set and said radiology image data;

generating 1140 a cartilage damage perimeter CDP based on said radiology image data;

generating 1160 a set of data representing a geometrical object based on said first surface, said second surface and said CDP, wherein said geometrical object represent identified cartilage damage, wherein said geometrical object is confined by said first surface, said second surface and said CDP;

generating 1170 control software adapted to control a CAD or CAM system to manufacture a surgical kit for cartilage repair dependent on said set of data representing a geometrical object and on a predetermined model of components of said surgical kit.

Figure 12:
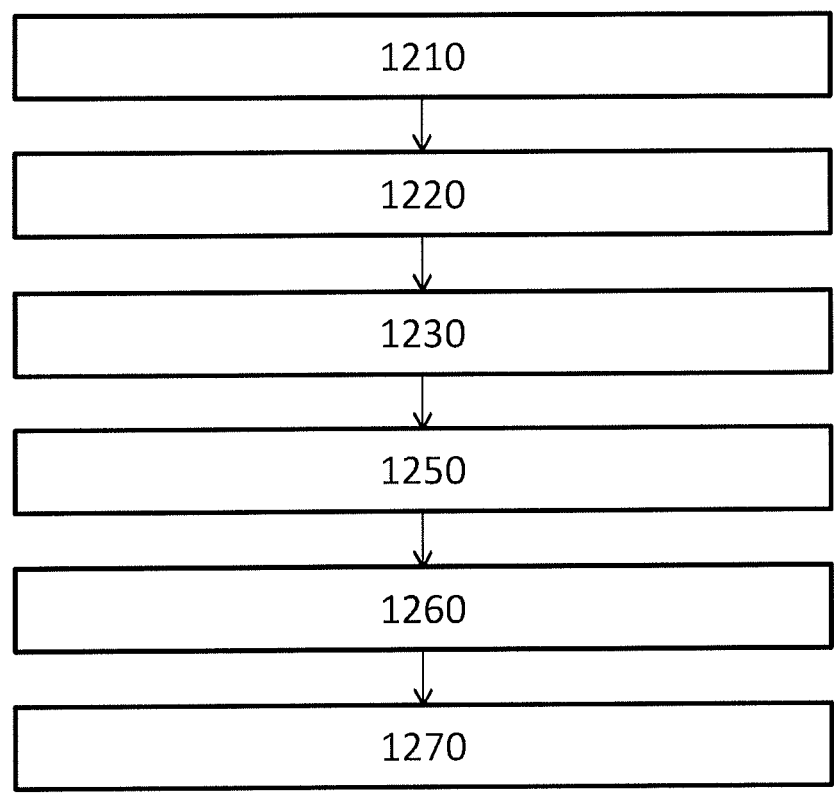
FIG. 12 shows a flowchart of yet an embodiment of a computer-implemented method to manufacturing a surgical kit for cartilage repair in an articulating surface of a joint.

FIG. 12 shows a flowchart of a computer-implemented method to manufacturing a surgical kit for cartilage repair in an articulating surface of a joint. In one or more embodiments, the method comprises the steps of:

receiving 1210 radiology image data representing three-dimensional image of a joint;

generating 1220 a first three dimensional representation of a first surface of the joint in a trainable image segmentation process dependent on a trained segmentation process control parameter set and said radiology image data;

generating 1230 a second three dimensional representation of a second surface of the joint in a trainable dynamical model process dependent on a trained dynamical model process control parameter set and said radiology image data;

generating 1250 a surgical kit perimeter SKP based on said radiology image data;

generating 1260 a set of data representing a geometrical object based on said first surface, said second surface and said SKP, wherein said geometrical object represent identified cartilage damage, wherein said geometrical object is confined by said first surface, said second surface and said SKP;

generating 1270 control software adapted to control a CAD or CAM system to manufacture a surgical kit for cartilage repair dependent on said set of data representing a geometrical object and on a predetermined model of components of said surgical kit.

Figure 13:
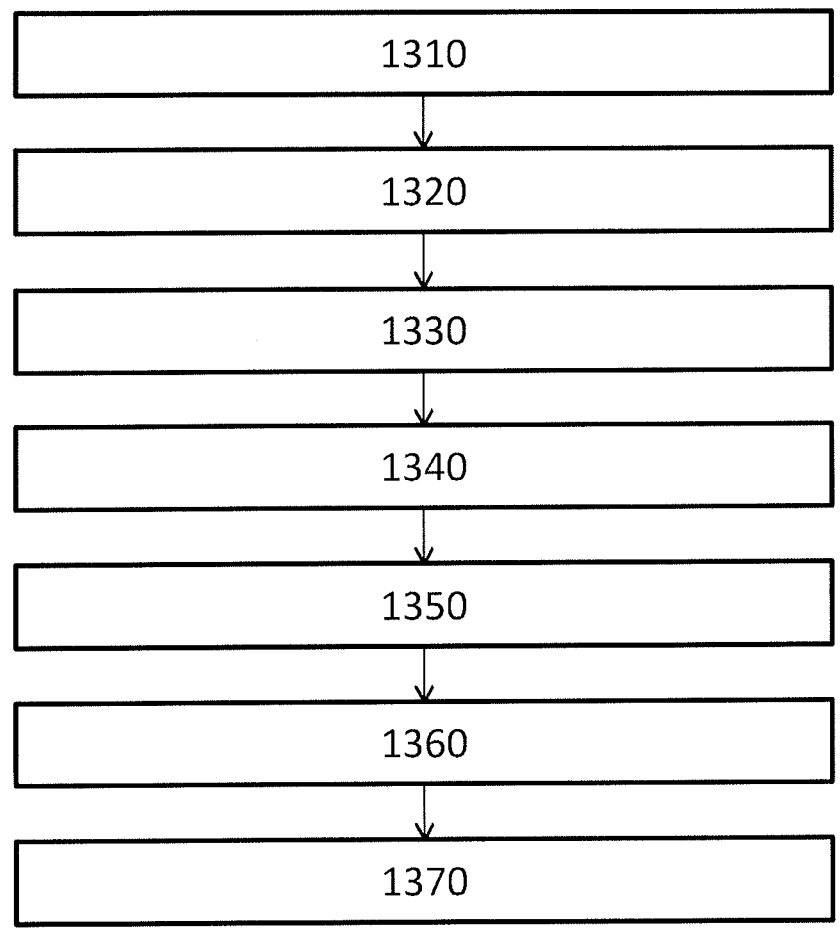
FIG. 13 shows a flowchart of yet an embodiment of a computer-implemented method to manufacturing a surgical kit for cartilage repair in an articulating surface of a joint.

FIG. 13 shows a flowchart of a computer-implemented method to manufacturing a surgical kit for cartilage repair in an articulating surface of a joint. In one or more embodiments, the method comprises the steps of:

receiving 1310 radiology image data representing three-dimensional image of a joint;

generating 1320 a first three dimensional representation of a first surface of the joint in a trainable image segmentation process dependent on a trained segmentation process control parameter set and said radiology image data;

generating 1330 a second three dimensional representation of a second surface of the joint in a trainable dynamical model process dependent on a trained dynamical model process control parameter set and said radiology image data;

generating 1340 a cartilage damage perimeter CDP based on said radiology image data;

generating 1350 a surgical kit perimeter SKP based on said radiology image data;

generating 1360 a set of data representing a geometrical object based on said first surface, said second surface, said SKP and said CDP, wherein said geometrical object represent identified cartilage damage, wherein said geometrical object is confined by said first surface, said second surface, said SKP and said CDP;

generating 1370 control software adapted to control a CAD or CAM system to manufacture a surgical kit for cartilage repair dependent on said set of data representing a geometrical object and on a predetermined model of components of said surgical kit.

In one or more embodiments, the implant design center system comprises a processor unit (e.g., a processor, microcontroller, or other circuit or integrated circuit capable of executing instructions to perform various processing operations)

In one or more embodiments, an implant design center with non-transitory machine-readable medium on which is stored machine-readable code that, when executed by a processor of a remote inspection system, cause the processor to perform the methods described herein.

In one or more embodiments, a computer program product comprising computer readable code configured to, when executed in a processor, perform any or all of the method steps described herein.

Where applicable, various embodiments provided by the present disclosure can be implemented using hardware, software, or combinations of hardware and software. In addition, where applicable, the various hardware components and/or software components set forth herein can be combined into composite components comprising software, hardware, and/or both without departing from the spirit of the present disclosure. Where applicable, the various hardware components and/or software components set forth herein can be separated into sub-components comprising software, hardware, or both without departing from the spirit of the present disclosure. In addition, where applicable, it is contemplated that software components can be implemented as hardware components, and vice-versa.

Software in accordance with the present disclosure, such as non-transitory instructions, program code, and/or data, can be stored on one or more non-transitory machine-readable mediums. It is also contemplated that software identified herein can be implemented using one or more general purpose or specific purpose computers and/or computer systems, networked and/or otherwise. Where applicable, the ordering of various steps described herein can be changed, combined into composite steps, and/or separated into sub-steps to provide features described herein.

Embodiments described above illustrate but do not limit the invention. It should also be understood that numerous modifications and variations are possible in accordance with the principles of the invention. Accordingly, the scope of the invention is defined only by the following claims.

The invention claimed is:

1. A method of manufacturing a surgical kit for cartilage repair in an articulating surface of a joint, comprising the steps of:

receiving radiology image data representing a three-dimensional image of a joint;

generating a first three-dimensional representation of a first surface of the joint in a trainable image segmentation process dependent on a trained segmentation process control parameter set and said radiology image data;

generating a set of data representing a geometrical object based on said first surface of the joint, wherein said geometrical object is confined by said first surface of the joint; and controlling a computer aided manufacturing (CAM) system to manufacture a surgical kit for cartilage repair dependent on said set of data representing a geometrical object and on a predetermined model of components of said surgical kit, wherein the trainable image segmentation process includes:

obtaining an initial segmentation process control parameter set as a previously used and stored segmentation process control parameter set;

generating the first three-dimensional representation of the first surface of the joint based on the initial segmentation process control parameter set, wherein the first three-dimensional representation of the first surface of the joint is evaluated by generating a three-dimensional representation quality value; and generating the trained segmentation process control parameter set by iteratively updating the initial segmentation process control parameter set until said three-dimensional representation quality value exceeds a predetermined quality value, wherein the trained segmentation process control parameter set is usable as an initial segmentation process control parameter set for generating one or more other three-dimensional representations of an articulating surface of a joint, based on different radiology data.

2. The method of claim 1, further comprising:
generating a second three-dimensional representation of a second surface of the joint in a trainable dynamical model process dependent on a trained dynamical model process control parameter set and said radiology image data,
wherein generating a set of data representing a geometrical object includes generating said set of data based on said second three-dimensional representation, wherein said geometrical object is further confined by said second surface.

3. The method of claim 2, wherein generating a second three-dimensional representation of a second surface of the joint in a trainable image segmentation process further comprises the steps:
I) obtaining an initial dynamical model process control parameter set;
II) determining a trained dynamical model process control parameter set as said initial dynamical model process control parameter set;
III) generating a second three-dimensional representation of said second surface based on said trained dynamical model process control parameter set and said radiology image data;
IV) determining a differential trained dynamical model process control parameter set based on a three-dimensional representation quality value, wherein said three-dimensional representation quality value is based on said second three-dimensional representation of said second surface of the joint generated based on said trained dynamical model process control parameter set and said radiology image data;
V) determining an updated trained dynamical model process control parameter set based on said trained dynamical model process control parameter set and said differential trained dynamical model process control parameter set; and
VI repeating steps I-V above if said three-dimensional representation quality value is below or above a predefined quality value threshold.

4. The method of claim 2, wherein the first surface of the joint is an underlying bone, and the second surface of the joint is aligned to undamaged cartilage tissue outer surface.

5. The method of claim 1, further comprising:
generating a cartilage damage perimeter (CDP) based on said radiology image data,
wherein generating a set of data representing a geometrical object includes generating said set of data based on said CDP, wherein said geometrical object is further confined by said CDP.

6. The method of claim 1, further comprising:
generating a surgical kit perimeter (SKP) based on said radiology image data,
wherein generating a set of data representing a geometrical object includes generating said set of data based on said SKP, wherein said geometrical object is further confined by said SKP.

7. The method of claim 1, wherein generating a first three-dimensional representation of a first surface of the joint in a trainable image segmentation process further comprises the steps:
obtaining a predefined number of instances of a trained segmentation process control parameter set;
for each instance of the trained segmentation process control parameter set:
generating a three-dimensional representation of said first surface of the joint based on the respective instance of said trained segmentation process control parameter set and said radiology image data, and
storing the generated three-dimensional representation of the first surface of the joint in a data buffer; and
determining an updated trained segmentation process control parameter set based on a first three-dimensional representation quality value, wherein said first three-dimensional representation quality value is based on said three-dimensional representations stored in the data buffer, said predefined number of instances, and a predetermined object function.

8. The method of claim 1, wherein generating a first three-dimensional representation of a first surface of the joint in a trainable image segmentation process further comprises the steps:
I) obtaining an initial segmentation process control parameter set;
II) determining a trained segmentation process control parameter set as said initial segmentation process control parameter set;
III) generating a first three-dimensional representation of said first surface of the joint based on said trained segmentation process control parameter set and said radiology image data;
IV) determining a differential trained segmentation process control parameter set based on a first three-dimensional representation quality value, wherein said first three-dimensional representation quality value is based on said first three-dimensional representation of said first surface of the joint, generated based on said trained segmentation process control parameter set and said radiology image data, and a predetermined object function;
V) determining an updated trained segmentation process control parameter set based on said trained segmentation process control parameter set and said differential trained segmentation process control parameter set; and
VI) repeating steps III-VI above if said first three-dimensional representation quality value is below or above a predefined quality value threshold.

9. The method of claim 1, wherein said radiology image data is based on a selection of X-ray, ultrasound, computed tomography (CT), nuclear medicine, positron emission tomography (PET) and magnetic resonance imaging (MRI).

10. A non-transitory computer readable memory on which is stored computer readable code configured to, when executed in a processor, perform the method steps of claim 1.

11. An implant design center system for manufacturing a surgical kit for cartilage repair in an articulating surface of a joint, the system comprising:
a memory;
a communications interface; and
a processor coupled to the memory and communications interface, the processor configured to perform the steps of:
receiving radiology image data representing a three-dimensional image of a joint;
generating a first three-dimensional representation of a first surface of the joint in a trainable image segmentation process dependent on a trained segmentation process control parameter set and said radiology image data;
generating a set of data representing a geometrical object based on said first surface of the joint, wherein said geometrical object is confined by said first surface of the joint; and controlling a computer aided manufacturing (CAM) system to manufacture a surgical kit for cartilage repair dependent on said set of data representing a geometrical object and on a predetermined model of components of said surgical kit, wherein the trainable image segmentation process includes:

obtaining an initial segmentation process control parameter set as a previously used and stored segmentation process control parameter set;

generating the first three-dimensional representation of the first surface of the joint based on the initial segmentation process control parameter set, wherein the first three-dimensional representation of the first surface of the joint is evaluated by generating a three-dimensional representation quality value; and generating the trained segmentation process control parameter set by iteratively updating the initial segmentation process control parameter set until said three-dimensional representation quality value exceeds a predetermined quality value, wherein the trained segmentation process control parameter set is usable as an initial segmentation process control parameter set for generating one or more other three-dimensional representations of an articulating surface of a joint, based on different radiology data.

12. The implant design center system of claim 11, wherein the processor is further configured to perform the steps of:

generating a second three-dimensional representation of a second surface of the joint in a trainable dynamical model process dependent on a trained dynamical model process control parameter set and said radiology image data, wherein generating a set of data representing a geometrical object includes generating said set of data based on said second three-dimensional representation, wherein said geometrical object is further confined by said second surface.

13. The implant design center system of claim 12, wherein the first surface of the joint is an underlying bone, and the second surface of the joint is aligned to undamaged cartilage tissue outer surface.

* * * * *